United States Patent [19]

Linner et al.

[11] Patent Number: 4,619,257

[45] Date of Patent: Oct. 28, 1986

[54] APPARATUS AND METHOD FOR CRYOPREPARING CORNEAL TISSUE FOR SURGICAL PROCEDURES

[75] Inventors: John G. Linner; John D. Goosey, both of Houston, Tex.

[73] Assignee: Board of Regents, The University of Texas System, Austin, Tex.

[21] Appl. No.: 676,856

[22] Filed: Nov. 30, 1984

[51] Int. Cl.$^4$ .............................................. A61B 17/36
[52] U.S. Cl. ................................................. 128/303.1
[58] Field of Search ............ 128/303, 303.1, DIG. 27, 128/24 A; 62/64, 78, 514 R

[56] References Cited

U.S. PATENT DOCUMENTS

| | | | |
|---|---|---|---|
| 2,672,032 | 3/1954 | Towse | 128/303.1 |
| 3,067,589 | 12/1962 | Dennis et al. | 128/303.1 |
| 3,125,096 | 3/1964 | Antiles et al. | 128/303.1 |
| 4,201,319 | 5/1980 | Anders et al. | 128/DIG. 27 |
| 4,336,691 | 6/1982 | Burstein et al. | 128/DIG. 27 |

*Primary Examiner*—Robert Peshock
*Assistant Examiner*—Wenceslao J. Contreras
*Attorney, Agent, or Firm*—Arnold, White & Durkee

[57] ABSTRACT

This invention relates to apparatus and the method for preparing corneal tissue for surgical graft, implantation or transplantation referred to herein as "surgical techniques" or "surgical procedures." Use of the apparatus and method for preparing the corneal tissue avoids significant modification of the ultrastructure of corneal tissue during preparation of the tissue samples themselves.

14 Claims, 12 Drawing Figures

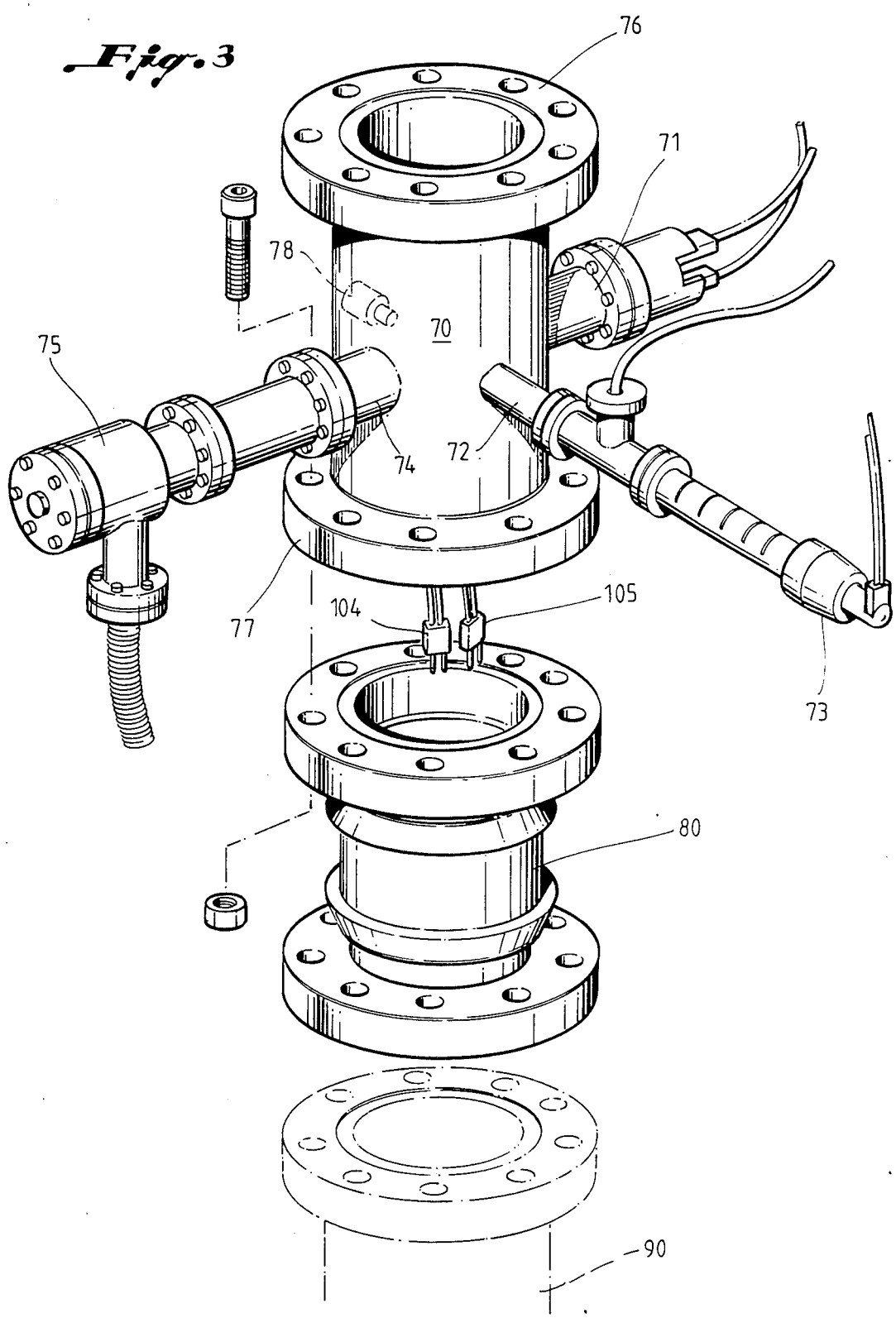

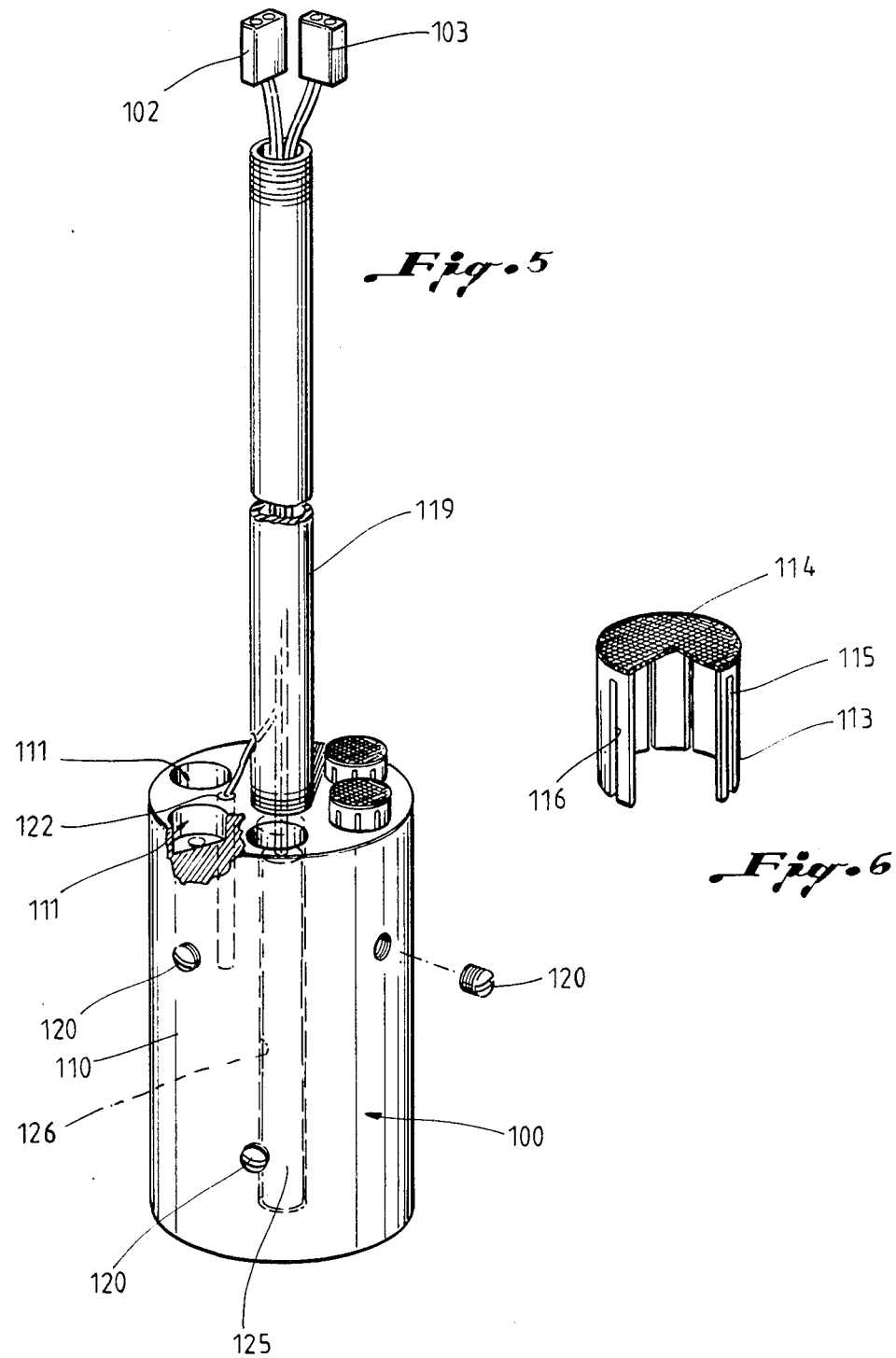

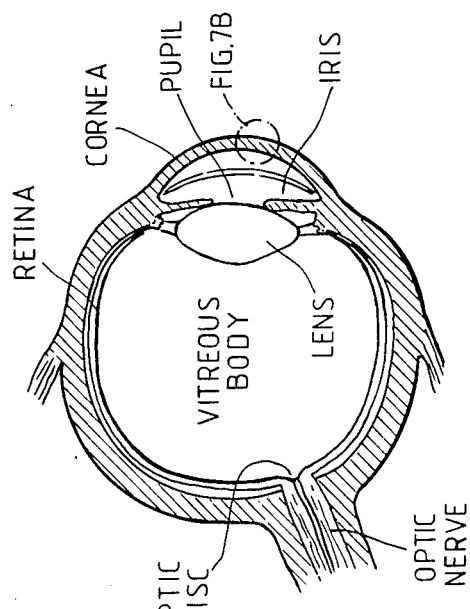
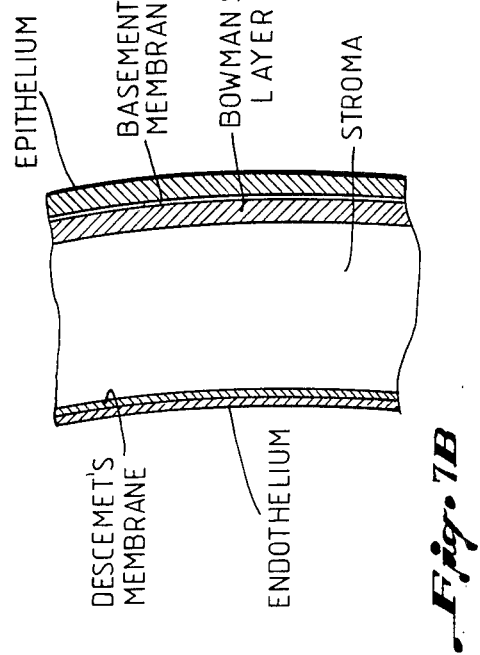
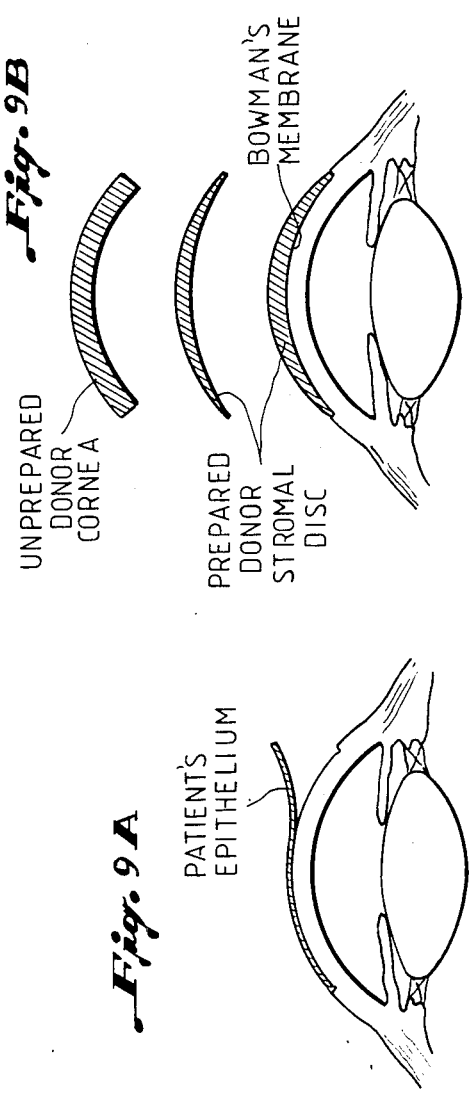
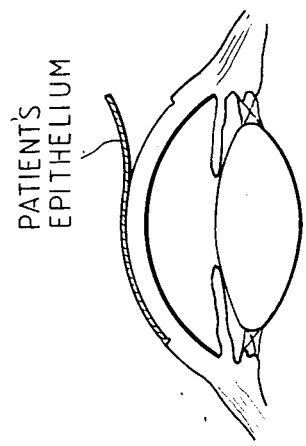
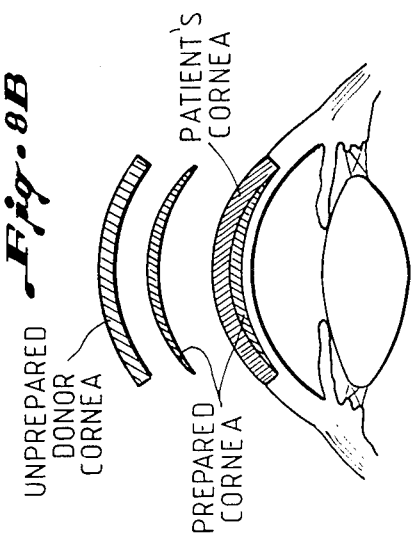
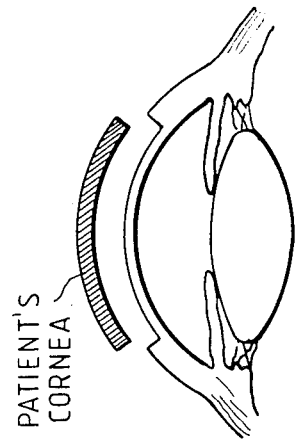

APPARATUS AND METHOD FOR CRYOPREPARING CORNEAL TISSUE FOR SURGICAL PROCEDURES

BACKGROUND OF THE INVENTION

1. Field of the Invention

This invention relates to apparatus and the method for preparing corneal tissue for surgical graft, implantation or transplantation referred to herein as "surgical techniques" or "surgical procedures." Use of the apparatus and method for preparing the corneal tissue avoids significant modification of the ultrastructure of corneal tissue during preparation of the tissue samples themselves.

Although the phrases "corneal tissue" and "corneal tissue samples" are used throughout this disclosure it should be understood that the terms are intended to include reference to corneal tissue as well as other ocular tissue that may be suitable for grafting, implantation or transplantation. Current medical technology has verified that corneal tissue is ideal tissue for surgical use. It is possible now to even cryo-lathe corneal tissue to achieve the desired parameters for visual correction in the patient.

The contemplated utility of the apparatus of this invention is not limited to specific types or sizes of tissue, rather it should be understood to refer to any tissue made up from cells. The apparatus of this invention can be designed or adapted to any size, shape or type of cellular tissue. Therefore, the terms "tissue" and "tissue samples" are used interchangeably and are not limiting on the uses to which the method and apparatus of this invention can be placed. It should further be understood that when the terms "tissue" or "tissue samples" are used the reference is to corneal tissue.

Historically, it has been very difficult to retain donor corneas for use in future surgical techniques because of the inherent loss of viability and contamination that occurs during the conventional tissue maintenance, retention and preparation processes. It is thus essential that these be avoided wherever possible.

The "preparation" of corneal tissue should be understood to refer to preparation of tissue for analysis as well as the cryofixation of tissue in anticipation of grafting, implantation, transplantation, or modification. The apparatus of this invention can be used to prepare tissue for any medical or analytical procedure without the ultrastructural damage previously thought to be inevitable in cryopreparation.

The apparatus of this invention is to be distinguished from contemporary freeze-drying apparatus. Freeze-drying is a technique which is well known in the art together with the equipment necessary to implement such freeze drying. See, for example, U.S. Pat. No. 4,232,453. Freeze-drying normally contemplates sample temperatures of −50° C. to −80° C. In contrast, the cryopreparation of this invention contemplates sample temperatures of −120° C. or below.

Conventional technology for maintaining and preserving corneal tissue prior to transplantation is by use of what is referred to in the technology as the McCarey-Kaufman media. The McCarey-Kaufman tissue media typically will maintain the viability of corneal tissue for approximately 4 to 5 days. The primary advantages of the McCarey-Kaufman media technique are its simplicity and expense as well as the ability to transport the tissue sample from one area to another. However, the obvious drawback is the short term (4 to 5 days) preservation of the corneal tissue.

The critical need to expand the 4 to 5 day preservation period to a substantially longer timeframe has resulted in some corneal surgeons using cryopreparation techniques for maintaining corneal tissue in a viable state prior to its use in transplantation surgery or other surgical procedures. Existing cryopreparation technology, much of which has been described hereinabove and will be described hereinbelow, includes a slowly controlled freezing of tissue and maintenance of the tissue in liquid nitrogen. These conventional cryopreparation techniques offer an advantage of long term storage but the critical disadvantage of inherent damage to the corneal tissue. The corneal tissue is damaged by ice crystal formation during both the freezing the thawing process. It is also inconvenient and difficult to transfer the tissue in a liquid nitrogen media.

The cryopreparation technique which is the subject of this disclosure offers the distinct advantage of long term preservation and at the same time eliminates the disadvantages of tissue deterioration and destruction due to ice crystallization and transportation.

As disclosed hereinbefore, the formation of ice crystals and artifacts during freezing is kept to a minimum by the cryopreparation of the tissue and cryofixation in less than one second. No other available methodology for cryopreparation of corneal tissue involves the extremes of temperature and pressure and concomitant rapid heat transfer which are present in the process and apparatus of this invention. The term "artifact" refers to a product of artificial character due to extraneous agency. The net result of ultrastructural translation or damage to corneal tissue is that the tissue is not suitable for use in surgical techniques.

The corneal tissue is rapidly supercooled with a "bounce free" apparatus with the endothelial surface of the tissue facing the chilled metal block. Such a configuration of the corneal tissue during its initial vitrification insures that the tissue water within the corneal endothelium reaches the vitreous phase and that minimal ice crystal formation occurs in the corneal endothelium. The tissue is then dehydrated by the process of stimulated molecular distillation. Since all water has been removed from the corneal tissue before it is allowed to devitrify there is no danger of ice crystal formation with resultant ultrastructural damage during the thawing process as is the case in freeze drying techniques. In addition, once the tissue has been dried it can be maintained indefinitely under low vacuum or in a dry inert gas atmosphere. It is also feasible to transport the dried and cryoprepared corneal tissue from one area to another, typically under conditions of low vacuum or dry inert gas.

When the corneal tissue is being prepared for transplantation, the vacuum or dry inert gas is removed and the corneal tissue is rehydrated with a balanced salt solution for an effective time period, typically 15 to 20 minutes. The corneal tissue is then ready for use in surgical techniques, such as transplantation, according to the standard surgical procedures for corneal transplantation. Recent information on such surgical procedures is provided by textbooks such as Smolin, G. and Throft, R., *The Cornea, Scientific Foundations and Clinical Practice*, 437–464 (1983) and Casey, T. and Mayer, D., *Corneal Grafting, Principles and Practice*, 81–86 and 271–280 (1984).

In addition to preserving a full thickness cornea, the process of this invention as well as the apparatus used in the process of this invention can also be used to preserve partial thickness corneal tissue. Partial thickness corneal transplants are commonly referred to as lamellar transplants. Recently a great deal of interest has evolved concerning the use of lamellar corneal tissue (partial thickness corneal tissue) for the correction of myopia (nearsightedness), hyperopia (farsightedness) and keratoconus. Current techniques employed to obtain corneal tissue used for lamellar transplants involve the use of relatively slow freezing (10 to 30 seconds) using a carbon dioxide jet with concomitant formation of deleterious ice crystals within the cellular architecture.

By using the ultra-rapid cryopreparation technique of this invention the vitreous state of water is achieved within the substructure of the corneal tissue and thereby the ultrastructural damage and inherent artifact formation are avoided which are inherent in previous freeze drying techniques.

The extreme low temperatures and vacuums used in the practice of the apparatus of this invention have generated unique problems not associated with freeze-drying apparatus. For example, sealing devices such as squeezable O-rings made from elastomeric material do not function effectively at these anticipated cryopreparation temperatures and vacuums. Therefore, it is necessary that cryopreparation apparatus be designed to seal various structures at the extremes of temperature and pressure encountered, i.e., the sample chamber to the rest of the apparatus. This is but one example of problems which have been encountered in the design of and which are unique to cryopreparation apparatus. For purposes of this application the terms "cryopreparation" and "cryofixation" are used in distinction to conventional "freeze drying" technology (−50° to −80° C.).

The vacuum levels disclosed and used in the apparatus of this invention cannot be achieved safely with prior art freeze drying equipment. Typical of previous methods for drawing vacuums in freeze drying methods and apparatus is the above-mentioned U.S. Pat. No. 4,232,453 which discloses the use of molecular sieves in glass containers. Molecular sieves in easily compromised containers cannot be used safely to create and maintain the required vacuum levels to achieve the partial pressures required for sublimation of water at the anticipated temperatures (−120° C. or below) created by the apparatus of the disclosed invention.

2. The Prior Art

Inherent in prior art processes for corneal tissue preparation is the concomitant damage to and deleterious modification of viable tissue characteristics. These tissue characteristic modifications represent a severe limitation on their utility for corneal surgery.

Similarly, it is essential that cryopreparation methods and apparatus develop concurrently with other medical technology, i.e., surgical transplant techniques, bioengineering and biogenetics. In short, cryopreparation is an essential intermediate step in evolving processes using or analyzing cells or tissue. If cryopreparation apparatus does not evolve then the thrust of medical technology into unexplained and unexplored medical arts will be blunted. The apparatus of this invention represents the cryopreparation breakthrough that will permit research into the use and preparation of biological tissue to keep pace with other advances in medical technology.

The most common method for preparing corneal tissue is freeze drying cryofixed tissue. Freeze-drying following cryofixation is a well documented and well known technique for tissue preservation. It has several advantages. Freeze-drying results in a near-instantaneous arrest of cellular metabolism. There is also a stabilization and retention of soluble cell constituents through elimination of solvent contact with the sample. These are significant advantages to freeze-drying that have resulted in a great deal of research in attempting to apply cryofixation and freeze-drying techniques to known tissue preparation processes.

Unfortunately, freeze-drying technology inherently possesses a number of disadvantages relevant to tissue preparation methodologies. The primary disadvantage in currently available freeze-drying techniques and apparatus is the inherent formation of ice crystals. As can be readily appreciated, the formation of ice crystals destroys the ultrastructural integrity of the tissue sample being reviewed. The infrastructure is distorted and the cytoplasm becomes reticulated. The formation of ice crystals in the sample can also result in a change in pH within microcompartments of the tissue (eutectic formation) which possibly can result in abnormal tertiary conformation of macromolecules. There is also the possibility that proteins will denature and precipitate. These are but a few of the disadvantages which are inherent in the freeze-drying process.

This general topic is discussed in some detail together with other prior art methods in an article entitled *Freezing and Drying of Biological Tissues for Electron Microscopy*, Louis Terracio and Karl G. Schwabe, published in The Journal of Histochemistry and Cytochemistry, Volume 29, No. 9 at pp. 1021–1028 (1981). Problems associated with artifact formation are described in *Understanding the Artefact Problem in Freeze-Fracture Replication: A Review*, The Royal Microscopial Society, (1982) at pp. 103–123.

The application of cryogenics to surgical procedures and specifically ocular surgical procedures is not entirely new. See for example U.S. Pat. No. 3,942,519 which discloses ultrasonic and cryogenic instrumentation adapted for the removal of cataracts in surgical operations. In addition, see U.S. Pat. No. 4,056,855 which discloses a method for implanting an intraocular lens. The patent mentions the historical use of cryogenic probes to remove cataracts. Reference is also made to U.S. Pat. No. 4,336,691 disclosing a "Cryojet Rapid Freezing Apparatus" which can be used to rapidly freeze specimens such as corneal endothelium. The freezing in U.S. Pat. No. 4,336,691 is typically for the purpose of electron microscope examination and not transplantation.

A general principle found applicable to freezing techniques, which has demonstrated utility in the preparation of tissue samples, is that as the cooling rate increases, tissue fluids can be vitrified without the separation of water to extracellular spaces. It has been postulated, that regardless of the rate of cooling, ice crystals may still be formed, but as the cooling rates increase the size of the intracellular ice crystals decreases. The small size or absence of ice crystals at high freeze rates is of course a substantial advantage in morphology retention as this results in minimal artifact creation and minimal ultrastructural damage during tissue dehydration. The apparatus of this invention requires the rapid supercooling of tissue samples to the vitreous phase in less than one second followed by dehydration of the tissue sample while in the state of reduced partial pressure of water vapor, all without substantial ultrastructural damage to the tissue cells.

Historically, the criteria by which the techniques for rapid supercooling have been judged was not the cooling rate of the system but simply the temperature of the environment in which the tissue was frozen. Thus, the term rapid supercooling has been applied to any system in which the supercooling agent has a temperature of $-150°$ C. or below. The effectiveness of a cooling system is dependent upon the rate at which heat is removed from the sample. Heat transfer is dependent not only on the temperature of the freezing system but also on its physical and thermal characteristics, as well as the size and thermal characteristics of the tissue.

The most commonly used technique for rapid supercooling is to immerse or "quench" the sample in a fluid cooling bath. The most commonly used fluids for quenching are liquid nitrogen, isopentane, propane and fluorocarbons such as Freon 12 and Freon 22. Although liquid nitrogen is generally regarded as an ideal quenching fluid due to its low temperature ($-196°$ C.), there are inherent disadvantages in the use of liquid nitrogen due to the occurrence of tissue surface film boiling caused at least in part by the low heat of vaporization of liquid nitrogen. Film boiling is a characteristic of liquid nitrogen that inhibits the heat transfer rates by actually insulating the sample.

An alternate prior method for rapid supercooling is freezing on the polished surface of a chilled metal block. This typically involves opposing the tissue sample to a polished flat metal surface by pressing it firmly against the surface of the metal. Silver and copper are typically used as the polished metal blocks. This method is designed to take advantage of the high thermal conductivities and heat capacities of these metals when cooled to liquid nitrogen or liquid helium temperatures. The critical step in chilling on the surface of a metal is making firm contact with the dry, chilled metal surface with no rotational, translational or rebounding motion. Certain commercially available apparatus having known utility in the medical arts address and provide "bounce-free" freezing. Credit for the development of this apparatus is generally accorded to Dr. Alan Boyne of the University of Maryland School of Medicine.

There has recently been verification that there is a direct correlation between cooling rate and ultrastructural preservation in quenching fluids. As the freezing rate increases over the range of 100° C. to 4100° C. per second (liquid nitrogen—propane), there is a corresponding decrease in the size of ice crystals formed and thus an improvement in morphological preservation. Use of such quenching fluids or other supercooling apparatus to vitrify a tissue sample in less than 1 second is preferred.

The critical steps in the subsequent tissue preparation process are invariably stimulated sublimation—dehydration of the supercooled tissue fluids, which have recently been described as a stimulated "molecular distillation" process. Once the appropriate supercooling method has been chosen and implemented, it is sometimes necessary to further process the corneal tissue.

For penetrating or full thickness transplantation the corneal tissue can be dehydrated with the apparatus of this invention and then stored or maintained for subsequent rehydration and transplantation. When refractive lamellar transplantation methodologies are indicated (epikeratophakia or keratomileusis) the cryoprepared corneal tissue may be modified by cryo-lathing the tissue so that its radius of curvature corresponds to an optical power appropriate to achieve visual rehabilitation. After these modifications are made it is then necessary to dehydrate the tissue with no concomitant ice crystal formation.

Thus, dehydration is an essential step in the preparation of biological tissue samples for storage. This step oftentimes results in tissue destruction via reticulation of the infrastructure if not performed under cryogenic conditions as disclosed. Tissue cell destruction from dehydration adversely affects the functional characteristics and viability of tissue masses being used, i.e. transplanted.

In certain prior drying techniques, the tissue sample had not been entirely solidified due to eutectic formation as the cellular fluid solutes were concentrated in bound water compartments. This transfer of solute occurs while the materials are in the fluid state when slow cooling is employed. When rapid cooling techniques are used, unique procedures which are distinct from those characteristic of freeze-drying, must be employed in the dehydration step. Problems result from the fact that dehydration must take place (the water must be removed) in the solid rather than the liquid state, i.e., via sublimation. An alternate procedure which has been used successfully is stimulated molecular distillation. Stimulated molecular distillation refers to a process in which the amount of energy in the antibonding orbitals of surface molecules is elevated, enabling them to escape to the gas phase and not be recaptured by the solid phase.

In the prior art, the freeze substitution approach has involved the removal of tissue water by substituting a solvent or solvent-fixative mixture for the solid phase water at $-50°$ to $-80°$ C. This introduces less severe solvent phase separation and chemical alteration artifacts to a tissue sample than past routine chemical fixation methodologies. From a practical standpoint freeze-drying is complicated by the requirement that the tissue sample be warmed to increase the vapor pressure of the supercooled water and allow sublimation to proceed in a reasonable period of time. The increased temperature, in addition to increasing vapor pressure can produce a series of physical events leading to the expansion of ice crystals and concomitant damage to the ultrastructural morphology of the tissue sample. Many of the physical events which occur during the warming process have to do with transitions in the physical state of the water which is present. Changes which are typically encountered are glass transition, devitrification and recrystallization with an ensuing series of crystal lattice configuration transitions.

Thus it can be appreciated that freeze-drying technology and cryopreparation techniques present an exceptional opportunity for the preparation of tissue samples for surgical techniques, i.e. grafting, implantation or transplantation. However, inherent in the use of freeze-drying techniques are problems associated with dehydration of samples. These are the problems which are addressed by the process and apparatus of this invention.

The cryopreparation process of this invention has demonstrated an extraordinary application in the transplanting of corneal tissue. Prior to this invention attempts to transplant corneas which involved a necessary freezing or freeze-drying of the corneas after removal from the donor invariably resulted in a clouded cornea upon transplanting. This physical condition of the transplanted cornea was caused by crystal formation in the cornea itself and concomitant damage to the stroma. Use of the apparatus of this invention has enabled ophthalmologists to cryoprepare corneas and to then transplant those corneas to recipients with virtually negligible clouding or crystal formation. The ability to so transplant corneas represents an exceptional advantage to the process of this invention as well as a medical breakthrough in corneal transplant surgery.

One advantage of the apparatus of this invention is the ability to cryoprepare tissue without overt disruption or destruction of the morphological characteristics of the ultrastructure of tissue cells. The apparatus of this invention permits the cryopreparation of tissue by dehydrating tissue maintained in the solid, vitreous phase without creating unnecessary artifacts.

DESCRIPTION OF THE DRAWING

FIG. 3 is an exploded schematic drawing of the portion of the apparatus of this invention connecting the vacuum means to the sample chamber.

FIG. 5 is a schematic view of the sample holder of this invention.

FIG. 6 is a schematic view of the tissue reservoir cover used in the sample holder of this invention.

FIGS. 7A and 7B are schematic cross-sectional views of the tissue components of the human eye. FIG. 7A is supplied so that reference to various eye components and eye tissue are understood. One section of the eye of FIG. 7A has been exploded as FIG. 7B to identify the layers of the cornea.

FIGS. 8A and 8B are schematic cross-sectional views of tissue laminations used in keratorefractive surgery.

FIGS. 9A and 9B are schematic cross-sectional views of tissue laminations used in epikeratorefractive surgery.

SUMMARY OF THE INVENTION

Figure 1:
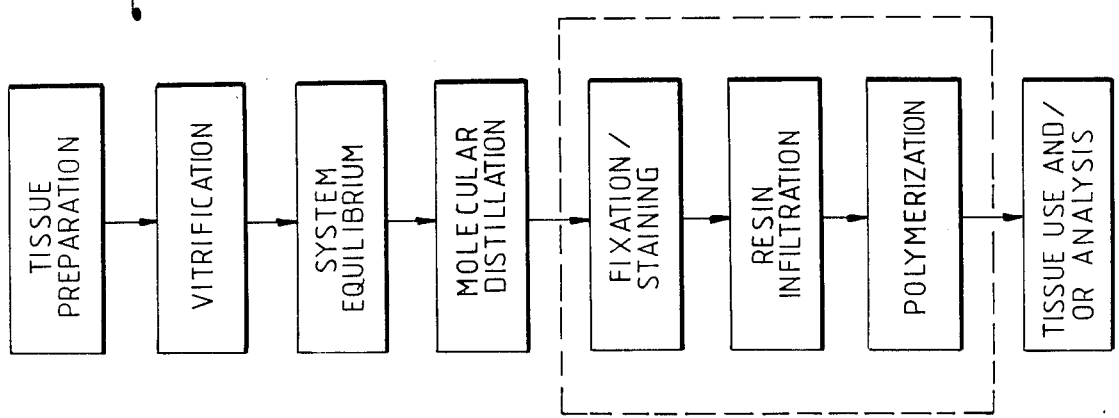
FIG. 1 is a schematic flow diagram of a method associated with the use of the apparatus of this invention.

This invention relates to apparatus and the method for the cryopreparation of corneal tissue samples. The apparatus includes components for implementing the stimulated dehydration of biological tissue under severely depressurized conditions. The depressurized, vitrified tissue sample is brought to equilibrium at a temperature of less than $-140°$ C. The tissue sample is then dehydrated while maintained in a state of equilibrium.

The apparatus of this invention includes a sample holder for retaining vitrified biological tissue. The sample holder and the vitrified tissue are maintained at cryogenic temperatures while the tissue sample is being dehydrated. Ultra-high vacuum means are used to depressurize the atmosphere of the sample holder to permit the desired sublimation; equilibration and dehydration procedures.

The apparatus of the invention is used in combination with conventional apparatus to vitrify biological tissue. The preferred vitrifying apparatus is a metal rod adapted to transform the tissue to the vitreous phase at a temperature of $-123°$ C. or below. The vitrified tissue is inserted in a sample holder which is fittably received by a sample chamber which in turn can be inserted or withdrawn from a cryogenic bath.

The ultra high vacuum assembly used to depressurize the sample chamber provides a pressure of from $1 \times 10^{-8}$ Torr to $1 \times 10^{-10}$ Torr. The ultra-high vacuum assembly is removably attached to the sample chamber.

In practice the apparatus of this invention is used to cryoprepare corneal tissue for surgical graft, implantation or transplantation. The apparatus is adaptable to an infinite variety of tissue shapes, sizes and configurations. The apparatus of this invention results in the cryopreparation of corneal tissue resulting in a final product whose ultrastructure is substantially unmodified and which is ready for end uses which have been heretofore impossible in the medical arts.

Corrective corneal surgery is accomplished using a variety of techniques. Several techniques involve the use of donor corneas or the modification of the patients natural cornea. Two common techniques are illustrated by FIGS. 8A–8B and 9A–9B. FIGS. 8A–8B represents schematically keratorefractive surgery which involves the placement of a donor lamellar disc of known curvature into a lamellar pocket in the patient's own cornea. FIGS. 8A–8B represent schematically epikeratorefractive surgery, which involves the removal of the patients epithelium preparing a groove in Bowman's layer and the suturing of a lyophilised donor stroma onto the surface.

In modifying either the patient's cornea or a donor cornea a cryolathe is used to grind the corneal tissue to the desired thickness, curvature and size. In the past corneal tissue has been frozen before cryolathing. Using a microtome the stroma of the cornea is ground to the required curvature. As explained hereinabove, such freezing inherently involves ultrastructural damage to the corneal tissue resulting from ice crystal formation. Improvements to the surgeon's ability to prepare, use and modify corneal tissue using the process and apparatus of this invention have been both dramatic and unexpected.

DESCRIPTION OF THE PREFERRED EMBODIMENT

In the apparatus of this invention it is a fundamental prerequisite that the desired tissue is obtained. Tissue samples are collected by a variety of means, i.e., surgical extraction, withdrawn blood samples, binders and any of a variety of other techniques which are well known and conventional. The particular method of obtaining the biological sample is not limiting on the apparatus of this invention. However, the preparation of the tissue sample in the apparatus of this invention is enhanced if the tissue sample is processed as soon after excising as is possible.

Corneal tissue samples are obtained from whole corneas using surgical trephines with diameters varying from 3 to 11 millimeters. This yields disk shaped corneal preparations with diameters corresponding to that of the surgical trephine. The thickness of the tissue samples varies from 0.1 millimeters to 1.0 millimeters. In a full corneal transplant the sample thickness is preferably from 0.4 millimeters to 0.7 millimeters while in lamellar transplants the sample thickness is preferably from 0.1 to 0.3 millimeters. Excess tissue, not harvested for eventual cryopreparation, may be used to obtain tissue typing. This ability to type corneal tissue and store it will be pertinent to the success of high risk corneal transplants.

The preparation of the tissue sample takes place immediately as it is received. The tissue sample cannot be retained in a fixative, i.e., formaldehyde, or another biologically active stabilizing solution, in an attempt to maintain the sample during shipping, storage or other necessary operations. It is also critical that the sample not be routinely frozen or otherwise physically modified prior to preparation according to the method of this invention.

In one application of the apparatus of this invention a tissue sample is prepared for use in one of several surgical techniques. The corneal tissue to be used in the method and apparatus of this disclosure must be vitrified as soon as possible. By vitrifying or vitrification it is intended to make reference to a process which results in cryofixation of the sample which is different from "frozen." In the process of vitrifying, the cooling apparatus which is used renders the sample in the vitreous phase such that soluble and insoluble moities contained in the tissue sample are not disturbed, translated, or altered nor are they concentrated (as eutectics). By definition, a vitrified liquid will shatter when undergoing a shear stress, e.g., window glass. The vitreous phase involves the conversion of liquid water into an amorphous or "glass" phase. This is accomplished by rapidly supercooling the tissue sample by opposing it "bounce-free" onto the highly polished (mirror-like) condensate-free surface of a metal rod maintained at about $-196°$ C. These operations have been discussed previously in the prior art section of this disclosure. It is preferred that such rapid-supercooling be completed in less than one second.

Of particular utility in the process and apparatus of this invention is a "bounce-free" freezing apparatus which has been identified in association with Dr. Alan Boyne of the University of Maryland School of Medicine. In this freezing apparatus, a copper block is used to vitrify the corneal tissue sample. This vitrification in conjunction with a supercooled fluid such as liquid nitrogen, helium, propane or the various freons will cause the tissue sample fluids to supercool to the amorphous state before and/or without the formation of noticeable or resolvable cell water ice crystals. It is desirable in the preferred embodiment that the now vitrified tissue sample be maintained at a temperature of less than about $-120°$ C. and preferably less than $-140°$ C. during storage and transfer operations prior to removal of the tissue water.

Temperature control is essential to prevent ice crystallization. It is thought that ice crystallization begins to occur at about $-123°$ C. This is, however, dependent on the chemical constituents of the cellular water. Applicant has therefore selected $-140°$ C. as the preferred temperature. It should be understood that the desired result is to maintain the temperature below that at which ice begins to crystallize and that $-123°$ C. and $-140°$ C. have been selected based on current experimentation. Therefore, for purposes of this application, the preferred tissue sample temperature to be maintained is below $-123°$ C. while the more preferred temperature is below $-140°$ C. and the most preferred temperature is $-196°$ C. or below.

Depending on the anticipated time lag between supercooling of the sample and dehydration of the sample, it may be stored submerged in a liquid nitrogen dewar. Once the sample has been dried properly it may be stored virtually indefinitely without cytoplasmic reticulation or other forms of cellular catabolism which will cause modifications and crystal lattice transitions resulting in undesirable artifacts which render the tissue virtually unusable in surgical procedures.

After vitrifying, and while maintaining the corneal tissue sample at a temperature of less than $-140°$ C. it is transferred via a specimen transport and fed to a specimen holder in vacuo. The specimen holder (also commonly referred to as a sample holder) is maintained in a temperature controlled container. The container and specimen holder are both preferably maintained at temperatures below $-140°$ C. In the most preferred embodiment of this invention, liquid nitrogen temperatures of $-196°$ C. are maintained. The reason that $-140°$ C. is preferred is that pure water, existing in the vitreous phase when at liquid nitrogen temperatures, will begin to initiate cubic ice crystallization at $-123°$ C. As discussed in the prior art section of this disclosure, ice crystallization causes ultrastructural damage, i.e., reticulation to the morphology of tissue samples.

Next, the atmosphere surrounding the tissue sample, specimen holder and container is depressurized. This is typically done by drawing a vacuum on the sample holder with conventional mechanical vacuum apparatus. The vacuum is drawn to a level of $3 \times 10^{-9}$ Torr in less than 300 minutes. In other embodiments of this invention, the vacuum which is drawn is from $1 \times 10^{-8}$ Torr to $1 \times 10^{-10}$ Torr accomplished in less than 300 minutes. These pressures remain at approximately $3 \times 10^{-9}$ Torr throughout the remainder of the prescribed routine until all the tissue water has been removed. Throughout equilibration of the system (10-100 hours), the corneal tissue temperature is maintained by liquid nitrogen or other suitable cooling means while the vacuum is being drawn and maintained.

At this time the tissue sample is at ultra low pressure and exceptionally low equilibrium cryo-temperature. After equilibration is obtained (with equilibrium temperature below $-140°$ C.), the vitreous water which is found in the tissue sample will begin to sublime as energy equal to the heat of sublimation is intermittantly and incrementally supplied to the sublimation front found in the tissue. This is a slow process but one which is critical to the preparation of the sample. It is an important requirement that the sample be permitted enough time to allow it to reach equilibrium after each addition of energy. By equilibrate it is meant that the temperature of the tissue sample no longer changes over a 1 to 5 hour time period and preferably a 2 to 4 hour time interval. In a typical corneal tissue preparation process the sample is rapidly vitrified to $-196°$ C. and maintained below $-140°$ C. during storage/transfer to the sample holder in the sublimation (drying) apparatus. After appropriate equilibration time the equilibrium temperature will be somewhere between $-140°$ C. and $-196°$ C. During this entire equilibration process a critical ultra-low pressure is maintained at $3 \times 10^{-9}$ Torr or below.

After the equilibration process, it would take an exceptional length of time for any appreciable amount of water to evaporate from the sample if no energy (heat) of sublimation were added to the system. Estimates are in terms of years for the water to evaporate at temperatures and pressures which are associated with the method of this invention. Therefore, in the most preferred embodiment of this invention, a secondary energy source (heating) is added to excite the sublimating water molecules without causing damage to the ultrastructure of the dry tissue sample. Radiant photon energy, having a particular wavelength, is thought to be an especially useful approach to accomplish this goal. Sublimation energy via microwave, laser systems and magnetic energy are also appropriate. The most preferred secondary source is the nuclear magnetic resonance or electron spin resonance approach in combination with the above. At equilibrium, the temperature of the tissue will not change unless the ambient parameters of the immediate environment (radiant energy predominates, i.e., room temperature is 27° C.) change. This is the general identification of the end point of system equilibrium.

Subsequent to the tissue sample reaching equilibrium, it is necessary to remove the supercooled solid water and/or presently unresolvable ice crystals (20 nanometers diameter or less) which have formed in the tissue during the vitrification operation. This portion of the dehydration process is absolutely critical and is the step where most potential disruption and reticulation of the ultrastructure in the tissue will express itself. This is accomplished by gradually replacing the energy of sublimation in the sample by minimal increments of stimulation energy per hour. The optimal condition is to have no tissue temperature increases.

By so raising the thermal energy equivalent to the latent heat of sublimation all of the solid water, whether micro-ice crystals or amorphous supercooled water, is effectively removed from the tissue sample by the surrounding cryosystem. This drying may be accomplished at temperatures between $-150°$ C. and $-80°$ C. This regimen of greater temperature latitude will provide variable results and is possible due to elevation of devitrification temperatures by the solutes that are dissolved in cell water at varying concentrations. With appropriate instrumentation, i.e. residual gas analyzers, it is possible to determine when all cell water has been removed. At that point, the energy increase can be accelerated to produce a final specimen temperature 3° C. above room temperature (28° C.-30° C.). Thus, with this instrumentation a significant advantage in the process of this invention is obtained.

The now dehydrated tissue sample has been permitted to reach room temperature plus 3° C. Even though reaching room temperature the vacuum is maintained at the original exceptionally ultra-low levels as has the temperature surrounding the sample. Room temperature for purposes of this application should be understood to be approximately 24° C.-27° C. There may logically be variations in this temperature level.

A person of ordinary skill in the art can readily appreciate that control of temperature throughout the processes of vitrification, equilibration, sublimation and dehydration are essential. The precise temperatures at which the tissue is maintained and the rate that the tissue temperature is changed are crucial although varied for different cellular structures. A typical routine for a cell mass such as a cornea would require the initial vitrification of the cornea tissue at $-190°$ C. or below. The sample is immediately heated to $-150°$ C. in approximately 4 hours. During the equilibrium, sublimation, dehydration stage the tissue sample is heated from $-150°$ C. to $-70°$ C. in 60 hours (rate=1.333° C./hr.). The drying process begins at approximately $-119°$ C. and is completed before devitrification at $-80°$ C. The sample is then heated from $-70°$ C. to $+25°$ C. in 4 hours. Generally the sample is heated to slightly above room temperature to prevent water condensation from invading the sample.

Subsequent to these steps the tissue sample is brought to atmospheric pressure by slowly admitting dry inert gas through a port. While in the dry inert gas atmosphere, the corneal tissue is removed and placed in a partitioned container. The portion of the container which contains the dehydrated corneal tissue and inert gas, preferably nitrogen, is then sealed. On the opposite side of the septum which partitions the container, a sterile rehydrating solution is provided. Penultimate to surgical use the septum is broken so that the rehydrating solution contacts and rehydrates the dehydrated corneal tissue. After approximately 20 to 30 minutes of rehydration, the corneal tissue is ready for surgical transplantation. The storage container will be labeled with previously obtained tissue typing information.

A more complete description of the apparatus used to cryoprepare biological tissue, including corneal tissue, is found in commonly-assigned, co-pending application Ser. No. 676,855, filed on even date herewith now U.S. Pat. No. 4,567,847. Said application is entitled "Apparatus and Method For Cryopreparing Biological Tissue For Ultrastructural Analysis" and is incorporated herein by reference.

Other apparatus are available for the execution of this hierarchy, but none have produced the result expected as they do not incorporate in totality the required, defined parameters discussed earlier. The apparatus which is used in the practice of the method of this invention is illustrated schematically in FIGS. 2 through 6.

The rapid freezing attained by the apparatus of the Alan Boyne type is preferred to the practice of the process of this invention. Liqiud nitrogen and other types of quenching baths in conjunction with chilled metal applications are used in the process of this invention to the extent they provide the vitrified phase of cell water in less than one second. A liquid nitrogen quenching bath is used to lower and maintain the temperature of the tissue sample which is included in the tissue holder.

In designing the apparatus or in selecting the apparatus for use in the method of this invention, it is necessary to understand the effects of the exceptionally low temperatures and pressures on various materials. For that reason, portions of the apparatus of this invention used to treat the material while in the vitrified state are typically made from stainless steel. Other materials may well be equally viable. Likewise, portions of the apparatus of this invention are made from or coated with Teflon ®, a Dupont manufactured material which consists in a major portion of tetrafluorans.

Figure 2:
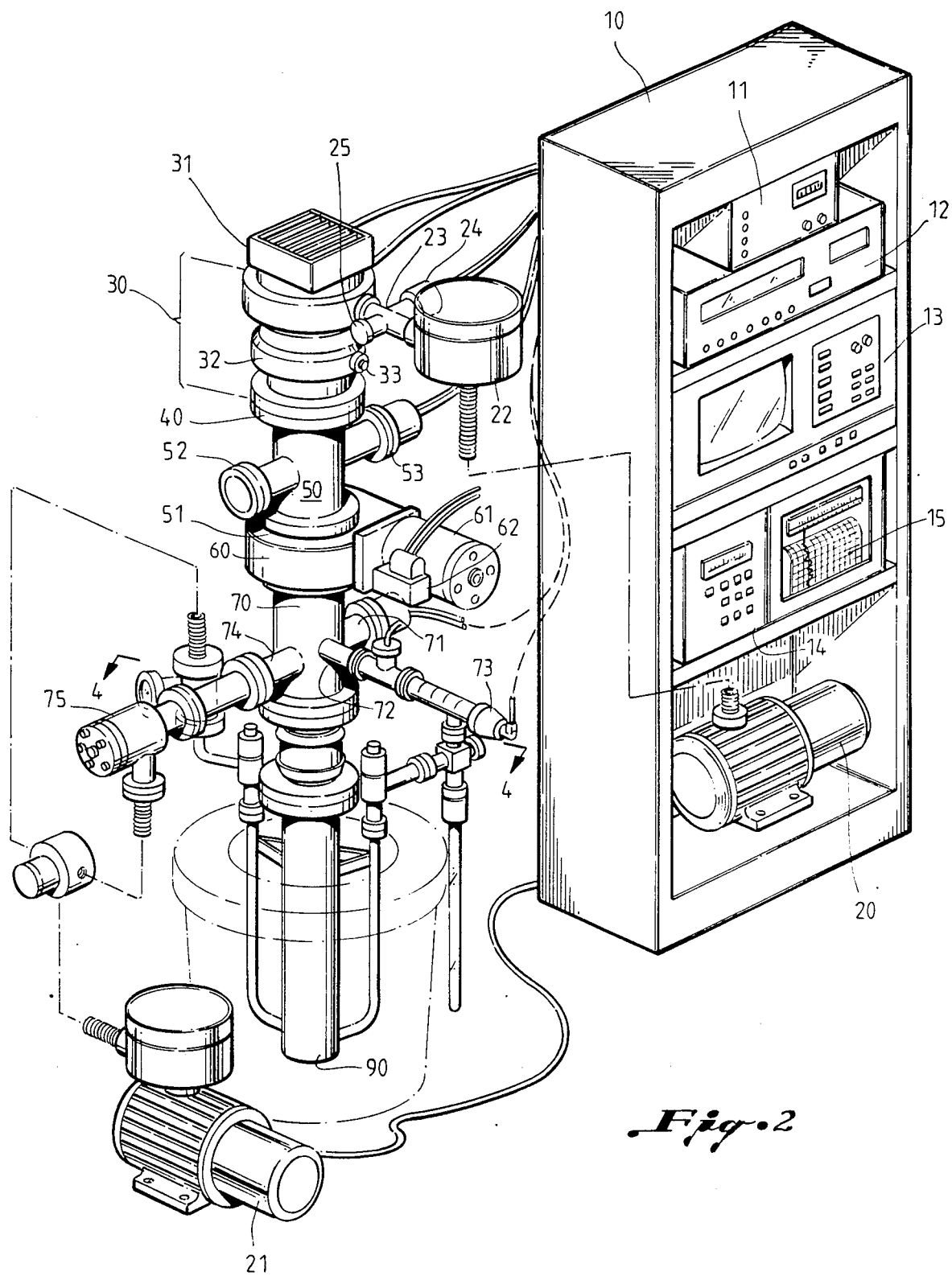
FIG. 2 is a schematic drawing of the apparatus of this invention.

FIG. 2 illustrates schematically the apparatus of this invention. As shown in FIG. 2, the apparatus is broadly categorized into a control panel 10 and the remainder of the apparatus used to vitrify, sublime and equilibrate the tissue. Microprocessor 11 of control panel 10 controls a turbomolecular pump 30. The control by microprocessor 11 is primarily of the revolutions per minute at which the components of the turbomolecular pump 30 are rotated and the temperature of the two main bearings in the turbo-molecular pump.

Digital vacuum gauge 12 of control panel 10 is connected to the apparatus in several places. In addition, the digital vacuum gauge 12 is attached to mechanical pumps to provide digital readings of both the low vacuum caused by the mechanical pumps and the ultra high vacuum caused by the turbomolecular pump.

The next component of control panel 10 is a residual gas analyzer 13. Residual gas analyzer 13 functions by reading the partial pressure of each gas in the sample chamber 90. Included in the analyzer 13 is a quadrapole mass spectrometer. This instrument can read the atomic weight of each gas present in the sample chamber 90. In addition, residual gas analyzer 13 is used to determine the water vapor levels in the chamber which can be used to determine the end point for dehydration.

Figure 4:
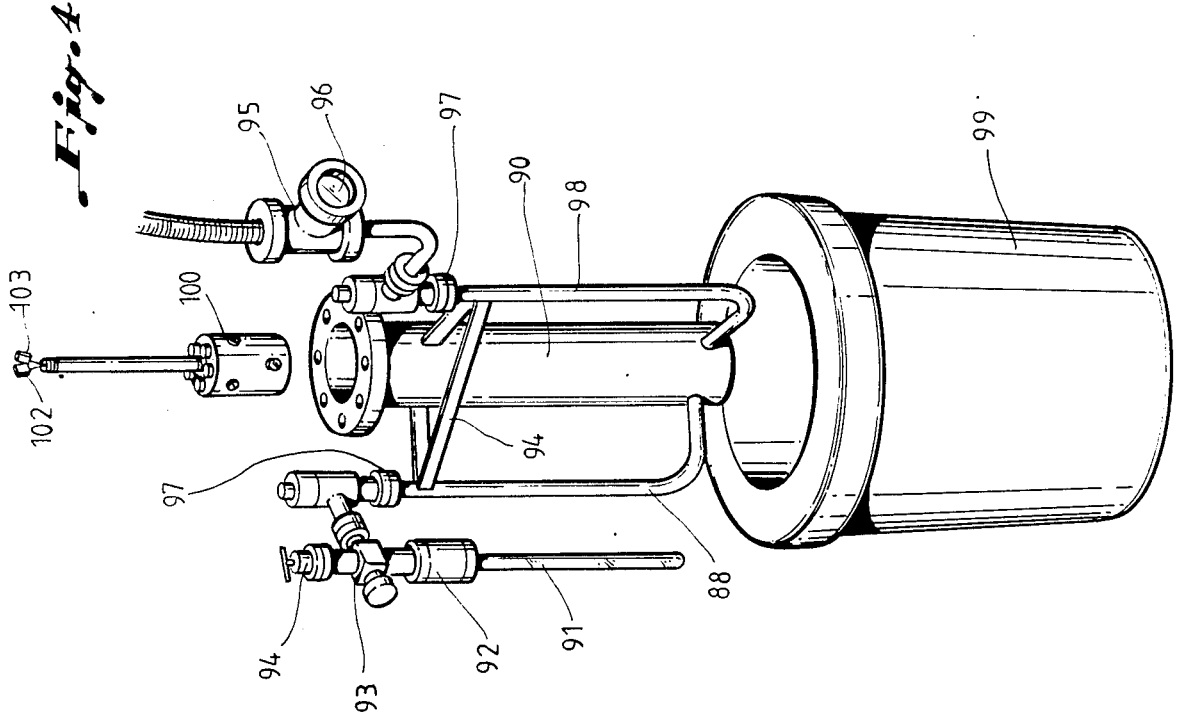
FIG. 4 is an exploded schematic drawing of the sample chamber and sample holder of this invention.

MIcroprocessor 14 is the component of control panel 10 used to read and control the temperature of the tissue samples in sample holder 100 (see FIG. 4). Microprocessor 14 reads the temperature of the metal supporting the tissue sample in sample holder 100 and does not contact the corneal sample itself. The programmable features of microprocessor 14 enable the implementation of a temperature control function as well as a temperature monitoring function.

Component 15 of control panel 10 is a chart recorder for microprocessor 14. Chart recorder 15 provides a graphic illustration of temperatures measured by microprocessor 14.

Mechanical pumps 20 (backing pump) and 21 (rough pump) are located in the control panel 10 as well as in conjunction with the main apparatus. Mechanical pump 20 is activated to draw the backing vacuum on the turbomolecular pump system. The initial vacuum is typically $1 \times 10^{-3}$ Torr. The mechanical pump 20 is also connected to molecular sieve trap 22 to trap any hydrocarbons that may be going back to the turbomolecular pump 30 from the mechanical pump 20. It is essential that no hydrocarbons reach the turbomolecular pump 30. The mechanical pump 20 and the molecular sieve trap 22 are arranged in series so that no hydrocarbons can bypass molecular sieve trap 22.

Molecular sieve trap 22 is connected to turbomolecular pump 30 by T connection 23. Low vacuum gauge head 24 extends from T connection 23 and is connected to the digital vacuum gauge 12.

In the preferred embodiment of this apparatus a solenoid valve 25 is connected to T connection 23 at the point illustrated by FIG. 2. The solenoid valve is used for a backing line (not illustrated) for dry nitrogen gas being connected to the turbomolecular pump 30. In the event that the vacuum or ultra-high vacuum system malfunctions and stops, the chamber is filled with inert nitrogen gas instead of moisture and hydrocarbon-containing air.

Turbomolecular pump 30 is used to create the ultra high vacuum of $1 \times 10^{-8}$ Torr to $1 \times 10^{-10}$ Torr required to properly practice the process of this invention. The ultra high pump 30 can be any of a variety of commercially available vacuum pumping apparatus. The preferred embodiment is a turbomolecular pump and in particular a turbomolecular pump manufactured by Leybold-Heraeus (Model TMP-360). It is essential that the ultra high vacuum pump, whether it is a turbomolecular pump or not, yield a hydrocarbon free vacuum. As mentioned previously, the mechanical pump 20 is used to pump out gases which are transmitted through the ultra high vacuum pump 30 from sample chamber 90.

In the preferred embodiment of this invention a cooling fan 31 is used to cool the bearings of the turbomolecular pump or other ultra high vacuum pump 30. A heating bakeout jacket 32 heats the walls of the ultra high vacuum pump 30 while in operation to ensure that gases are desorbed from the inner surfaces of the ultra high vacuum pump. These gases and even liquids are converted from condensation on the inner surfaces of the turbomolecular pump to result in gases thus enhancing the vacuum created by the turbomolecular pump 30. Thermocouple 33 provides the connection to the energy source (not shown) for heating bakeout jacket 32.

Conflat flange 40 is used to seal the turbomolecular pump to a first spool 50. Conflat is a trademark of Varian Industries, Inc. and describes a brand of flange. The type of flange associated with "Conflat" is well known to those skilled in the art and can generally be described as a first surface having a knife edge designed to penetrate a second abutting surface which is a soft metal. Although many state of the art sealing devices will function effectively to seal the members at the ultra high vacuums and temperatures desired, it has been found most preferable to use a 100 cf Conflat flange which is a stainless steel flange with a copper O-ring seal. Of great importance in Conflat flange seal 40 is the fact that is functions effectively at temperatures up to 150° C. during bakeout of the apparatus. This permits the effective formation of a seal with relatively standard sealing means. It would be virtually impossible to form the seal necessary if flange 40 were sealed with conventional, squeezable O-rings which are typically made from elastomeric material.

Spool 50 provides the conduit from the turbomolecular pump 30 to a gate valve 60. Spool piece 50 includes four Conflat flanges. The first is the common Conflat flange 40 with turbomolecular pump 30. The second is Conflat flange 51. The third and fourth Conflat flanges are identified by numerals 52 and 53. Conflat flange 52 connects spool 50 to the residual gas analyzer 13 sensing head while Conflat flange 53 provides the seal between the spool 50 and a Bayard-Alpert gauge.

An electropneumatic, ultra high vacuum pendulum gate valve 60 comprises the main valve isolating the turbomolecular pump 30 from the sample chamber 90. A piston contained within piston housing 61 provides the mechanism for opening and closing gate valve 60. Solenoid valve 62 and nitrogen gas are used to actuate the opening and closing of gate valve 60.

A second spool piece 70 is illustrated in FIG. 2 but in more specific detail by FIG. 3. Reference should be made to FIG. 3. Second spool piece 70 provides feedthrough from the pendulum gate valve 60 to the sample chamber 90. Spool piece 70 has extensions 71, 72, 74 and 78 connected to the main portion of the spool piece housing. Flange 71 provides tubulation for electrical feedthrough to the control panel 10 from the sample chamber 90. Flange 72 is tubulation for the low pressure vacuum head. At the exterior end of tube 72 is located low vacuum gauge head 73. Low vacuum gauge head 73 is connected to digital vacuum gauge 12. An ultra high vacuum valve 75 to mechanical pump 21 is located at the end portion of extension 74 from spool piece 70. The valve 75 acts to control the preliminary or "rough" vacuum drawn on sample chamber 90. Conflat flanges 76 and 77 are used to seal spool piece 70 to gate valve 60 and to ceramic insulator spool 80. The fourth extension from spool piece 70 is overpressure relief valve 78 shown by phantom line in FIG. 3.

Ceramic insulator spool 80 is inserted between spool piece 70 and sample chamber 90. Insulator spool 80 functions to prevent gross heat transfer from the elements of the apparatus above spool piece 70 to the cryogenic dewar 99 below (see FIG. 4). Without insulator spool 80 frost and ice frequently develop on the exterior of the ultrahigh vacuum pump assembly 30 and other connected elements. Ceramic insulator spool 80 also permits more efficient utilization of the supercooling material, i.e. liquid nitrogen.

The sample chamber 90 is used to retain the sample holder 100. These components are illustrated in FIGS. 4 and 5. Since the apparatus of this invention is also used to prepare tissue samples other than corneas for analysis by magnification apparatus resin embedding components are typically present in the apparatus. The sample chamber apparatus 90 includes a resin containing chamber 95 and a glass window 96 to provide visual access to the resin containing chamber 95. A gold sealed ultra high vacuum valve 97 and tubulation 98 to provide access for the resin into the sample chamber 90. Glass tube 91 is attached to sample chamber 90 via glass to metal adapter 92 and tubulation 88 which in turn is connected to a metal "T" flange 93. Calibrated leak valve 94 is used to flush or permeate the sample chamber 90 with dry nitrogen gas or other inert material. The tube 91 is used to include osmium tetroxide crystals for introduction of osmium vapors into the sample chamber 90 during staining operations. Support members 94 are used to maintain the relative spacing of tubulation 88 and 98 from the housing of sample chamber 90. Cryogenic dewar 99 is used to maintain the cryogenic cooling means, i.e., liquid nitrogen. The staining and fixation elements of the apparatus of this invention are not used during the cryopreparation of corneal tissue for surgical procedures.

In the most preferred embodiment of the apparatus of this invention a device is provided for sensing and automatically controlling the level of supercoolant, i.e. liquid nitrogen, in cryogenic dewar 99. Inherent in the use of liquid nitrogen or other similar coolants is the boiling off of the coolant over a period of time. Thus the coolant level must be periodically replenished to maintain the desired level of cooling. This can be accomplished manually or a mechanism can be installed for automatically sensing and replenishing the coolant level.

The sample holder 100, as shown in FIGS. 5 and 6, is used to retain the actual tissue samples. Typically the cryogenic bath environment 99 is liquid nitrogen contained by a dewar. The essential characteristic is that the tissue temperature must not exceed $-140°$ C. The thermoconductivity of the cryogenic energy from the cryogenic bath environment 99 to the sample holder 100 is inherent in the structure. Reference here is made specifically to FIG. 4.

In the most preferred embodiment of this invention radiant heating means 125 are provided to permit a source of radiant energy to the tissue samples. Typically the radiant heating means are controlled by rheostats or thermostats. Temperature indicating means such as identified as component 14 of control panel 10 are typically used so that the temperature of the environment and tissue samples can be specifically controlled. In the preferred embodiment of this invention the radiant heating means and temperature indicating means are all operated by a microprocessor of a computer within precise defined ranges.

Other forms of energy are equally useful with the apparatus of this invention. More particularly, electromagnetic energy sources such as microwaves, radio waves, accoustic sound waves, visual light waves and ultraviolet or near ultraviolet waves may be used. Magnetic flux is also useful, especially in combination with any of the above enumerated energy forms. Combinations of the above may be used depending on the application and sample to which the use of the apparatus is placed. Infrared radiation should be avoided. Sample characteristics are of paramount importance in determining the energy source which is ultimately selected.

In actual operation a tissue sample is vitrified to liquid nitrogen temperatures, i.e., less than $-140°$ C. The tissue is then transferred from a storage dewar to the sample holder 100 under liquid nitrogen temperatures with prechilled forceps.

The sample holder 100 is placed into the precooled sample chamber 90. Thermocouple with 102 extending from sample holder 100 is then connected to mating wire 104 extending down from spool piece 70 (see FIG. 3). Likewise, heater wire 103 is then connected to mating flow through wire 105 extending from spool piece 70. The specimen chamber 90 is then connected to the spool 70 via Conflat flange 77. This connection must be accomplished in the liquid nitrogen bath. Mechanical pump 21 is then activated and the spool 70 and sample chamber 90 are evacuated (rough pumped) to approximately $1 \times 10^{-3}$ Torr. The valves connecting the mechanical pump to sample chamber 90 is then closed and the main valve 60 between the turbomolecular pump 30 and sample chamber 90 is opened. At this time the drying process begins.

The system is allowed to thermally equilibrate while being constantly monitored by the instrumentation in control panel 10. The turbomolecular pump draws a vacuum of approximately $1 \times 10^{-8}$ Torr to $1 \times 10^{-10}$ Torr. The samples themselves are monitored by the residual gas analyzer 13 which includes a quadrapole mass spectrometer.

When the tissue is in equilibrium as indicated by no change in temperature for one to five and preferably two to four hours, the temperature controller is raised from $-150°$ C. to about $-70°$ C. Preferably the temperature is raised at a rate of $1°$ C. per hour to $3°$ C. per hour or more. In the most preferred embodiment the temperature is raised at a rate of from $1°$ C. per hour to $10°$ C. per hour. When the residual gas analyzer 13 shows no increase in water vapor after an increase in temperature the tissue is determined to be dry (typically at $-85°$ C. to $-70°$ C.). The temperature is then increased to $25°$ C. When the tissue has reached $25°$ C. the liquid nitrogen level in the dewar is allowed to drop and the outside walls of the sample chamber 90 are warmed to room temperature.

FIG. 1 is a schematic illustration of the process for use of the equipment of this invention. The portion of FIG. 1 which is included within a dotted line is not asserted to be new or novel, only the apparatus which is used to implement these steps is new and novel. By use of the apparatus of this invention, it is possible to achieve medical goals heretofore thought to be impossible.

Although the preferred embodiment of the apparatus of this invention has been described hereinabove in some detail, it should be appreciated that a variety of embodiments will be readily available to a person designing cryopreparation apparatus for a specific end use. The description of the apparatus of this invention is not intended to be limiting on this invention, but is merely illustrative of the preferred embodiment of this invention. Other apparatus and components which incorporate modifications or changes to that which has been described herein are equally included within this application.

It is essential to the proper functioning of the apparatus of this invention that the sample holder 100 be sized and designed to be fittably received by sample chamber 90 and to maintain one or more tissue samples in the proper condition of vitrification during equilibration, sublimation and dehydration. The sample holder 100, which has shown specific utility in the apparatus of this invention, is illustrated more specifically in FIGS. 4, 5 and 6.

Referring now specifically to FIG. 5, the sample holder 100 consists of a solid block of metal 110, preferably copper, silver, or gold, and combinations or alloys of copper, silver and gold. In the most preferred embodiment an alloy of silver and copper plated with gold is used. A plurality of wells 111 have been created in one surface of metal block 110. A central aperture 126 is also found in metal block 110. Radiant heat means 125 is inserted in aperture 126. The wells 111 create tissue reservoirs. The cryoprepared tissue samples are individually inserted into tissue reservoirs 111 with prechilled forceps as previously disclosed.

The tissue samples are then covered with reservoir cover 113. Reservoir cover 113 includes a wire mesh section 114 and a side wall 115. The configuration of reservoir cover 113 is shown with more specificity in FIG. 6. Wire mesh section 114 is attached to side wall 115 by special vacuum adhesives. Solder is not appreciated because of the out-gas properties of most solders. The finer the mesh 114 the more effective the desired gas transfer. Reservoir cover 113 also functions to protect the tissue samples from the effects of sudden changes in pressure such as when the gate valve 60 is opened or closed.

Teflon® spacers 120 are intermittently spaced around the exterior surface of solid metal block 110 to provide the proper spacing from the wall or other chilled surface of sample chamber 90. A Teflon® sleeve 119 is threaded into central aperture 126 to protect connecting wires 102 and 103. The thermocouple connection is found at 122 on the uppermost surface of sample holder 100. Although the sample holder 100 is shown in a size and configuration which is appropriate for cryopreparation of tissue samples for analysis, it should be understood that a person of oridnary skill in the art can equally prepare a sample holder to accommodate larger tissue masses or other forms of tissue.

In actual practice, individual tissue samples are placed in reservoirs 111 and reservoir cover 113 is inserted over the top of the tissue sample. As illustrated by FIG. 5, the covers 113 extend slightly above the surface of sample holder 100 to provide means for grasping the covers 113 during insertion or removal. In the most preferred embodiment of this invention slits 116 are provided in side wall 115 to give some flexibility to the covers 113, again to assist insertion and removal. The apertured surface 114 of covers 113 permits dehydration and sublimation without forming unnecessary moisture on the walls of reservoirs 112. It should also be understood that the preferred material for use in forming solid metal block 110 is copper although other materials, i.e. silver, gold, and alloys or combinations of copper, silver and gold, have been shown to be equally viable. The characterizing function of solid metal block 110 is the ability to transmit ultra low temperatures to the tissue samples and to maintain performance characteristics under the ultra high vacuum and ultra low temperature conditions of the cryopreparation apparatus and process of this invention.

Radiant heating means 125 are illustrated in FIG. 5 and provide a source of radiant heat to the tissue samples. Radiant heating means 125 are controlled by control panel 10. Control panel 10 permits infinite variability to the radiant heating means. In particular, temperature reader/recorder 14 and chart recorder 15 maintain information and control over the temperature of tissue reservoirs 112 and the tissue samples contained therein. As has been specifically pointed out hereinabove, control of sample temperature and the environmental temperature surrounding the tissue samples is absolutely essential to the effective functionality of the apparatus of this invention.

The most preferred embodiment of the sample holder 100 is illustrated in FIG. 5. Included in the most preferred embodiment is radiant heating means 125 which are shown in aperture 126. The most preferred form of radiant heating means 125 is a 220 volt/100 watt cartridge heater. The heating system is made more efficient by coating the interior, polished (spectral) surface of side wall 115 of reservoir cover 113 with a material which permits the efficient transfer of radiation energy to the specimen. Thus, in the preferred copper embodiment, the walls 115 are treated with potassium sulfide to turn the interior surface walls black and thus provide the mechanism for controlled radiant heating of the tissue sample. In some embodiments the interior surfaces of wells 111 are likewise spectral.

Thus, the radiant heating means, i.e. cartridge heater 125, is controlled by temperature reader/recorder 14. The heating mechanism is selectively activated manually or preferably by a programmable computer or microprocessor to maintain the desired temperature or temperature rate of change. Upon heating the metal block 110 conducts heat energy to the tissue reservoirs 112 and the heat energy is absorbed by the spectral coating on reservoir cover 113 and/or side wall 115. The spectral coating then acts as the source of radiant heat to the tissue samples.

Although the preferred embodiment of the specimen holder of this invention has been described hereinabove in some detail, it should be appreciated that a variety of embodiments will be readily available to a person designing an apparatus for a specific end use. The description of the preferred sample holder of this invention is not intended to be limiting on this invention, but is merely illustrative of the preferred embodiment of this invention. Other specimen holders which incorporate modifications or changes to that which has been described hereinabove are equally included within this application.

What is claimed is:

1. A method for cryopreparing corneal tissue for use in surgical procedures comprising:
   (a) obtaining a corneal tissue sample and sizing said tissue sample for its intended end use;
   (b) vitrifying said corneal tissue sample;
   (c) bringing said vitrified corneal tissue sample to equilibrium at a temperature of less than $-140°$ C.; and
   (d) dehydrating said vitrified corneal tissue sample while said sample is maintained in a state of equilibrium.

2. The method of claim 1 further comprising the step of sealing said dehydrated corneal tissue sample in a container, the atmosphere surrounding said sample in said container including a substantial portion of an inert gas.

3. The method of claim 2 further comprising the step of rehydrating sid dehydrated corneal tissue sample.

4. The method of claim 1 wherein said corneal tissue sample is vitrified in less than one second.

5. The method of claim 1 wherein said dehydration is by means of sublimation.

6. The method of claim 1 wherein said vitrified corneal tissue sample is dehydrated under vacuum.

7. The method of claim 6 wherein said vacuum reaches from $1 \times 10^{-8}$ Torr to $1 \times 10^{-10}$ Torr.

8. The method of claim 1 wherein said corneal tissue sample is characterized by an average diameter of from 3 to 11 millimeters.

9. The method of claim 8 wherein said corneal tissue sample is characterized by an average thickness of from 0.1 to 1.0 millimeters.

10. A method for cryopreparing corneal tissue for use in surgical procedures comprising:
    (a) obtaining a corneal tissue sample, said sample being characterized by an average diameter of from 3 to 11 millimeters and an average thickness of from 0.1 to 1.0 millimeters;
    (b) vitrifying said corneal tissue sample in less than one second;
    (c) bringing said vitrified corneal tissue sample to equilibrium at a temperature of less than $-140°$ C.; and
    (d) dehydrating said vitrified corneal tissue sample by sublimation and under vacuum while said corneal tissue sample is maintained in a state of equilibrium.

11. The method of claim 10 further comprising the step of sealing said dehydrated corneal tissue sample in a container, the atmosphere surrounding said sample in said container including a substantial portion of an inert gas.

12. The method of claim 10 further comprising the step of rehydrating said dehydrated corneal tissue sample.

13. The method of claim 10 wherein said vacuum reaches from $1 \times 10^{-8}$ Torr to $1 \times 10^{-10}$ Torr.

14. A method for cryopreparing corneal tissue for use in surgical procedures comprising:
    (a) obtaining a corneal tissue sample, said sample being characterized by an average diameter of from 3 to 11 millimeters and an average thickness of from 0.1 to 1.0 millimeters;
    (b) vitrifying said corneal tissue sample in less than one second;
    (c) bringing said vitrified corneal tissue sample to equilibrium at a temperature of less than $-140°$ C.; and
    (d) dehydrating said vitrified corneal tissue sample by sublimation and under vacuum while said corneal tissue sample is maintained in a state of equilibrium, said vacuum reaching a level of from $1 \times 10^{-8}$ Torr to $1 \times 10^{-10}$ Torr;
    (e) sealing said dehydrated corneal tissue sample in a container, the atmosphere surrounding said sample in said container including a substantial portion of an inert gas; and
    (f) rehydrating said dehydrated corneal tissue sample.

* * * * *